United States Patent
Nakama et al.

(10) Patent No.: US 10,458,961 B2
(45) Date of Patent: Oct. 29, 2019

(54) GAS CHROMATOGRAPH

(71) Applicant: Shimadzu Corporation, Kyoto (JP)

(72) Inventors: Yuji Nakama, Kyoto (JP); Shigeaki Shibamoto, Kyoto (JP); Minoru Kashihara, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 185 days.

(21) Appl. No.: 15/665,753

(22) Filed: Aug. 1, 2017

(65) Prior Publication Data
US 2019/0041368 A1 Feb. 7, 2019

(51) Int. Cl.
G01N 30/32 (2006.01)
G01N 30/62 (2006.01)
G01N 35/10 (2006.01)
G01N 30/86 (2006.01)
G01N 30/60 (2006.01)
G01N 30/02 (2006.01)

(52) U.S. Cl.
CPC ............ G01N 30/32 (2013.01); G01N 30/62 (2013.01); G01N 35/1097 (2013.01); G01N 30/8658 (2013.01); G01N 2030/025 (2013.01); G01N 2030/324 (2013.01); G01N 2030/6013 (2013.01); G01N 2030/625 (2013.01); G01N 2030/628 (2013.01)

(58) Field of Classification Search
CPC .... G01N 30/32; G01N 30/62; G01N 30/8658; G01N 35/1097; G01N 2030/324; G01N 2030/628; G01N 2030/6013
See application file for complete search history.

(56) References Cited

U.S. PATENT DOCUMENTS

| | | | | |
|---|---|---|---|---|
| 3,174,326 A * | 3/1965 | Carle | ........................ | G01N 30/44 392/480 |
| 3,435,660 A * | 4/1969 | Sternberg | ................ | G01F 1/704 73/23.24 |
| 4,316,381 A * | 2/1982 | Woodruff | ............... | G01N 30/32 422/54 |
| 4,962,042 A * | 10/1990 | Morabito | ............... | G01N 30/14 422/89 |
| 5,339,673 A * | 8/1994 | Nakagawa | ............. | G01N 30/10 73/23.36 |

(Continued)

FOREIGN PATENT DOCUMENTS

JP S53-46091 A 4/1978

Primary Examiner — David J Bolduc
(74) Attorney, Agent, or Firm — Maier & Maier, PLLC

(57) ABSTRACT

Provided is a gas chromatograph including a column which separates a sample; a detector which is configured to alternately introduce a carrier gas containing a sample component separated by the column and a carrier gas alone into a detection unit by changing an inflow point of the carrier gas to acquire a signal; an analysis information input unit with which analysis information is input; a data retaining unit which retains data indicating a relationship between a column flow rate and a carrier gas flow rate which is obtained in advance; and calculation unit which is configured to calculate the carrier gas flow rate on the basis of the analysis information input from the analysis information input unit and calculate the carrier gas flow rate according to the calculated column flow rate by using the calculated column flow rate and the data retained in the data retaining unit.

4 Claims, 3 Drawing Sheets

(56) References Cited

U.S. PATENT DOCUMENTS

| | | | | |
|---|---|---|---|---|
| 5,391,221 | A * | 2/1995 | Fukushima | G01N 30/10 95/82 |
| 5,859,360 | A * | 1/1999 | Magni | G01N 30/32 73/19.05 |
| 6,357,277 | B1 * | 3/2002 | Pigozzo | G01N 30/8665 73/1.06 |
| 8,656,754 | B2 * | 2/2014 | Kawana | G01N 30/28 73/23.36 |
| 9,983,104 | B2 * | 5/2018 | Tipler | G01N 1/2226 |
| 2007/0183928 | A1 * | 8/2007 | Neyer | G01N 30/32 422/70 |
| 2010/0101411 | A1 * | 4/2010 | Tipler | G01N 30/20 95/86 |
| 2012/0118049 | A1 * | 5/2012 | Tipler | G01N 30/72 73/61.56 |
| 2012/0125444 | A1 * | 5/2012 | Tipler | G01N 30/40 137/14 |
| 2017/0356890 | A1 * | 12/2017 | Saito | G01N 30/02 |

* cited by examiner

GAS CHROMATOGRAPH

BACKGROUND OF THE INVENTION

Field of the Invention

The present invention relates to a gas chromatograph used for gas chromatography (GC).

Description of the Related Art

A thermal conductivity detector (TCD) is known as a detector used for gas chromatography. The thermal conductivity detector utilizes the transfer of heat between a heating element (filament) and a fluid (gas) flowing around the heating element. The gas is introduced into a space where the heating element is accommodated and then discharged from the space.

In general, the thermal conductivity detector is provided with at least two cell spaces where the filament elements are arranged. The filament elements are arranged in the respective cell spaces.

A reference gas flows in the one cell space. A carrier gas flows in the other cell space, and a sample gas to be analyzed is introduced in the other cell space. Then, electrical outputs of the two filament elements enter a detection circuit. In the detection circuit, a correction current flows according to a difference in thermal conductivity caused by the introduction of the sample gas. In the thermal conductivity detector, the sample is detected by detecting the correction current.

In addition, there is known a gas chromatograph having a detector that acquires a signal by controlling whether the sample gas separated by a column is introduced into the detection unit or the carrier gas alone is introduced into the detection unit according to a pressure difference generated by changing an inflow point of the carrier gas (refer to, for example, JP-A-53-046091).

FIG. 4 is a block diagram illustrating an overall gas chromatograph in the related art.

A carrier gas is stored in a storage tank 102. A flow rate regulator 104 is connected between a column 106 and the storage tank 102. A sample inlet 108 is connected to one end of the column 106. Herein, the column 106 has a function of separating each sample component in a time sequence manner.

A gas flowed out from the column 106 is transported in one direction in one of pipes 112 and 114 through a connecting portion 110. Namely, the gas flowing into the pipe 112 is transported to an outlet 118 through the coil-shaped pipe 116 and is discarded in the atmosphere.

On the other hand, the gas flowing into the pipe 114 is transported to a detector 122 through a coil-shaped pipe 120. The selection as to which pipe (112 or 114) the gas discharged from the column 106 is switched to flow into is performed by the method described below.

The carrier gas stored in the storage tank 102 is transported to pressure regulators 126 and 128 through the pipe 124. The gas flowed out from the pressure regulator 126 is transported to the pipe 112 through the valve 130. Herein, a connecting portion 132 between the valve 130 and the pipe 112 is located between the coil-shaped pipe 116 and the connecting portion 110.

In addition, the gas flowed out from the pressure regulator 128 is transported to the pipe 114 through a valve 134. Herein, a connecting portion 136 between the valve 134 and the pipe 114 is located between the coil-shaped pipe 120 and the connecting portion 110.

As illustrated in FIG. 1, when the valve 130 is opened and the valve 134 is closed, the pressure of the carrier gas in the connecting portion 132 is set to a predetermined pressure value by the pressure regulator 126. Herein, the predetermined pressure value denotes a pressure sufficient to transport the gas (mixed gas of the carrier gas and the sample gas) discharged from the column 106 to the detector 122 through the coil-shaped pipe 120.

On the other hand, when the valve 130 is closed and the valve 134 is opened, the pressure of the carrier gas in the connecting portion 136 is set to a predetermined value by the pressure regulator 128. Herein, the predetermined pressure denotes a pressure sufficient to flow the gas discharged from the column 106 to the outlet 26 through the coil-shaped pipe 116. Therefore, in this case (the valve 130: closed and the valve 134: opened), the carrier gas alone is introduced into the detector 122.

With the above-described switching unit, it is possible to select whether to introduce the carrier gas alone into the detector 122 or to introduce the sample gas from the column 106. In addition, the opening and closing control of the valves 130 and 134 is performed by a valve driving circuit 138.

The gas discharged from the column 106 and the carrier gas alone are alternately introduced into the detector 122. Therefore, a bridge output signal 140 of the detector 122 appears as an AC signal. Namely, a level difference between the bridge output signal 140 by the gas discharged from the column 106 and the bridge output signal 140 by the carrier gas alone is caused by each component of the sample. Therefore, in a case where the sample gas is not included, the two output signal levels become equal to each other.

Although the output voltage of the bridge output signal 140 gradually changes in level, it affects the above two signals in common. Therefore, by subtracting the bridge output signal level by carrier gas alone, a temporal drift of the detector 122 can be eliminated.

In JP-A-53-046091, it is controlled whether a sample gas is introduced into a detection unit or a carrier gas alone is introduced into the detection unit according to a pressure difference generated by changing the inflow point of a carrier gas.

In this method, when the sample gas is introduced into the detection unit, the sample gas is pushed toward the detection unit side with the carrier gas, so that the sample gas is diluted by the carrier gas, and the minimum detection amount is lowered.

The dilution of the sample gas becomes large when a carrier gas flow rate is increased (namely, the pressure is increased), and the dilution becomes small as the carrier gas flow rate is decreased (the pressure is lowered). Therefore, it is preferable to reduce the carrier gas flow rate.

However, in a case where the carrier gas flow rate is excessively reduced, the sample gas cannot be switched, and the sample cannot be measured. Therefore, it is important to specify an appropriate carrier gas flow rate (pressure).

However, since it was necessary for an operator to specify the carrier gas flow rate so far, an appropriate carrier gas flow rate was not specified. Therefore, there is a problem in that the dilution of the sample gas caused by the carrier gas is large and the minimum detection amount is lowered.

SUMMARY OF THE INVENTION

The invention is to provide an appropriate carrier gas flow rate to an operator.

According to an aspect of the invention, there is provided a gas chromatograph including: a column which separates a sample; a detector which is configured to alternately introduce a carrier gas containing a sample component separated by the column and a carrier gas alone into a detection unit by changing an inflow point of the carrier gas to acquire a signal; an analysis information input unit with which analysis information is input; a data retaining unit which retains data indicating a relationship between a column flow rate and a carrier gas flow rate which is obtained in advance; and a calculation unit which is configured to calculate the column flow rate on the basis of the analysis information input from the analysis information input unit and calculate the carrier gas flow rate according to the calculated column flow rate by using the calculated column flow rate and the data retained in the data retaining unit.

The gas chromatograph according to the embodiment of the invention can calculate an appropriate carrier gas flow rate and provide the carrier gas flow rate to the operator.

DETAILED DESCRIPTION OF THE INVENTION

In the gas chromatograph according to the embodiment of the invention, the analysis information is, for example, at least one of an inner diameter of the column, a length of the column, a temperature, and a pressure applied to the column. In addition, the analysis information is not limited to the information listed herein.

In addition, in the gas chromatograph according to the embodiment of the invention, the gas chromatograph is configured to display the calculated carrier gas flow rate on a display unit, to input a carrier gas at the calculated carrier gas flow rate, or to perform both.

An appropriate carrier gas flow rate (pressure) is determined by the shape of the gas flow path and the flow rate of the sample gas. A relationship between the appropriate carrier gas flow rate and the sample gas flow rate is obtained in advance by experiments or numerical calculation such as simulation and retained in an internal memory (data retaining unit) of the gas chromatograph according to the embodiment of the invention.

Herein, the relationship between the appropriate column flow rate and the carrier gas flow rate is a previously obtained relationship representing the carrier gas flow rate at which the detection signal becomes larger with respect to the column flow rate when the column flow rate is set as a variable. In addition, the carrier gas flow rate at which the detection signal becomes larger than the column flow rate is preferably a carrier gas flow rate at which the detection signal becomes maximum, but the carrier gas flow rate is not limited thereto. For example, the carrier gas flow rate in the relationship between the column flow rate and the carrier gas flow rate may be a carrier gas flow rate by which the detection signal has a certain size or more, for example, a carrier gas flow rate by which a detection signal of 90% or more of the maximum value of the detection signal can be obtained.

In the analysis using the gas chromatograph, the operator necessarily inputs analysis information, that is, information (inner diameter and length) of the column to be used, a temperature condition, a gas pressure to be applied to the column, and the like manually or automatically. The gas chromatograph according to the embodiment of the invention automatically calculates the sample gas flow rate (column flow rate) at the outlet of the column by using these values and obtains an appropriate carrier gas flow rate from the calculated column flow rate and the value retained in the internal memory (data retaining unit). By automatically displaying the obtained carrier gas flow rate on the display unit, it is possible to provide an appropriate carrier gas flow rate to the operator. Accordingly, it is possible to suppress dilution of the sample gas caused by the carrier gas and to improve the minimum detection amount.

Figure 1:
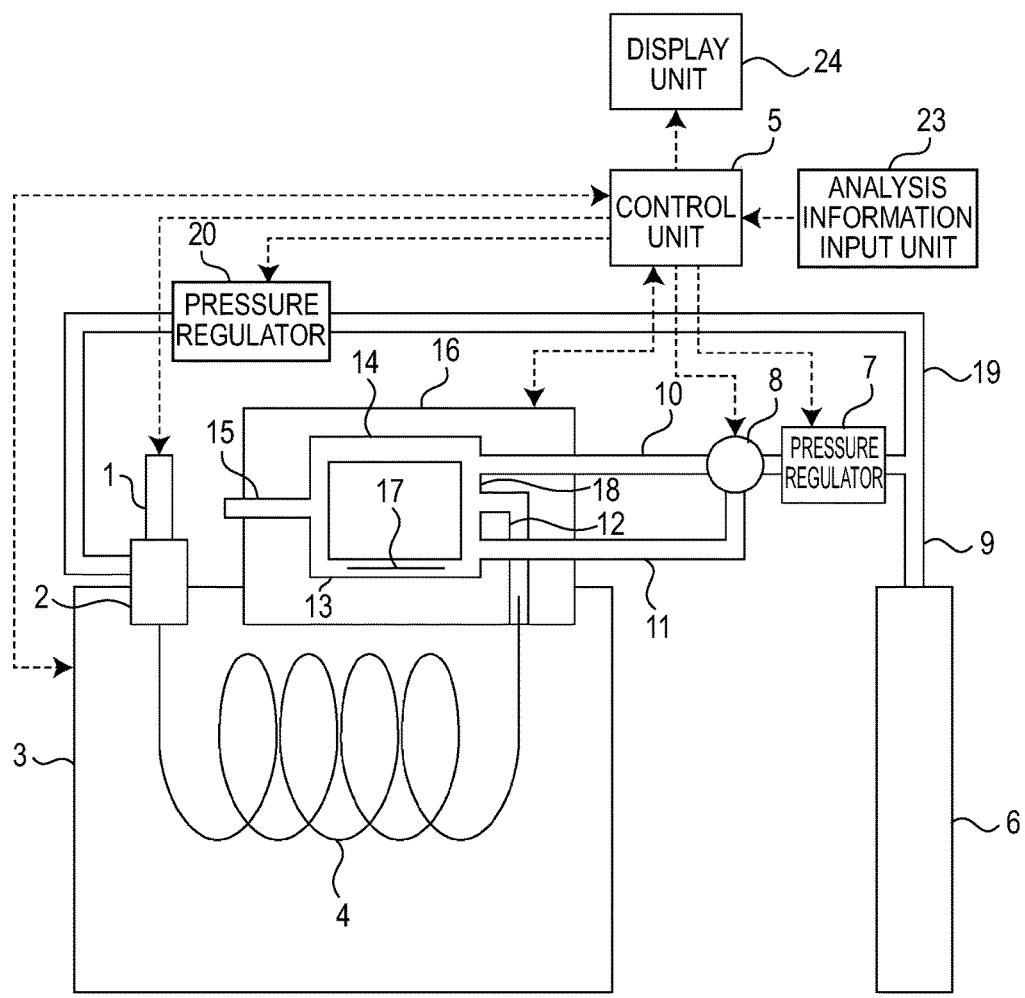
FIG. 1 is a schematic configuration diagram illustrating a gas chromatograph according to an embodiment.

FIG. 1 is a schematic configuration diagram illustrating a gas chromatograph according to an embodiment.

The analysis flow path of this gas chromatograph has a column 4 and a detector 16. One end of the column 4 is connected to a sample vaporizing chamber 2. The column 4 separates a sample which is introduced from an injector 1 into the sample vaporizing chamber 2 to be vaporized and is transported by the carrier gas. The column 4 is arranged inside a thermostatic bath 3. The other end of the column 4 is connected to a detector 16.

The detector 16 detects sample components separated by the column 4. The detector 16 is manufactured by, for example, a MEMS (Micro Electro Mechanical Systems) process. Therefore, a small-sized thermal conductivity detector can be realized. However, the detector 16 may be manufactured by a technique other than the MEMS technique, for example, one formed as a metal block, or the like.

The sample gas separated by the column 4 is transported in one direction in one of the flow path 13 in which the detection unit (filament) 17 is arranged and the flow path 14 where there is no detection unit (filament) through the flow path 12 and the flow path 18 in the detector 16. The gas introduced into the flow path 13 or the flow path 14 is discharged to the outside of the detector 16, for example, to the atmosphere through the flow path 15. The one end of the flow path 18 is connected to the flow path 13. The other end of the flow path 18 is connected to the flow path 14. The flow path 12 is connected to the flow path 18 at a position between the flow path 13 and the flow path 14.

A flow path to which the pipe 10 is connected and a flow path to which the pipe 11 is connected are also connected to the flow path 18. The flow path to which the pipe 10 is connected is connected to the flow path 18 at a position between the flow path 12 and the flow path 14. The flow path to which the pipe 11 is connected is connected to the flow path 18 at a position between the flow path 12 and the flow path 13.

The carrier gas stored in the tank 6 is transported to a pressure regulator 20 through a pipe 9 and a pipe 19. The carrier gas flowed out from the pressure regulator 20 is transported to the sample vaporizing chamber 2. The sample gas obtained by vaporizing the sample introduced from the injector 1 into the sample vaporizing chamber 2 is transported to the column 4 by the carrier gas and separated. The separated sample gas is transported to the detector 16 by the carrier gas.

Whether the sample gas flows into the flow path 13 or the flow path 14 in the detector 16 is determined by the following method.

The carrier gas stored in the tank 6 is also transported to the pressure regulator 7 through the pipe 9. The carrier gas flowed out from the pressure regulator 7 is transported to either the pipe 10 or the pipe 11 through a switching valve 8.

In a case where the carrier gas is transported to the pipe 10, the sample gas flowing out from the flow path 12 to the flow path 18 is pushed by the carrier gas flowed out from the pipe 10 and flows into the flow path 13 where the detection unit 17 is arranged. The carrier gas alone flows into the flow path 14 where there is no detection unit (filament).

On the contrary, in a case where the carrier gas is transported to the pipe 11, the sample gas is pushed by the carrier gas transported from the pipe 11 and flows into the flow path 14 where there is no detection unit (filament). The carrier gas alone flows into the flow path 13 where the detection unit 17 is arranged.

Whether to introduce the sample gas from the column 4 or the carrier gas alone into the flow path 13 where the detection unit 17 is arranged can be selected by a gas switching method using the pressure difference as described above. For example, by operating the switching valve 8 at a constant period of, for example, about 100 milliseconds, signals of the sample gas and the carrier gas can be acquired by the detection unit 17. A chromatogram of the sample gas can be obtained by taking the difference between the respective signals.

A control unit 5 is provided to control a column flow rate and a carrier gas flow rate. For example, the control unit 5 is configured to mainly include a microcomputer including a CPU (Central Processing Unit), a RAM (Random Access Memory), a ROM (Read Only Memory), an EPROM (Erasable Programmable ROM), and the like dedicated to a gas chromatograph provided in a gas chromatograph main body. The control unit 5 may be implemented by, for example, a workstation or a personal computer outside the gas chromatograph, other than the CPU and the like dedicated to the gas chromatograph. In addition, the control unit 5 may be configured with a plurality of CPUs, a plurality of work stations, a plurality of personal computers, a combination thereof, or the like.

An analysis information input unit 23 with which analysis information and the like are input to the control unit 5 is provided. For example, a display unit 24 which displays the analysis information and the carrier gas flow rate calculated by the control unit 5, and the like are provided.

The control unit 5 controls the operations of, for example, the injector 1, the thermostatic bath 3, the pressure regulator 7, the switching valve 8, the detector 16, and the pressure regulator 20.

Figure 2:
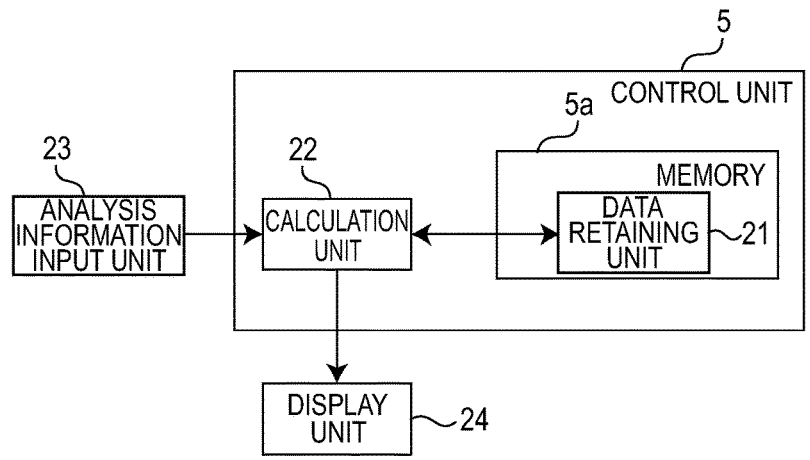
FIG. 2 is a schematic block diagram illustrating a carrier gas flow rate calculation function of a control unit according to the embodiment.

FIG. 2 is a schematic block diagram illustrating a carrier gas flow rate calculation function of the control unit according to the embodiment.

The configuration of the control unit 5 is, for example, a function executed by a program installed in the microcomputer and data retained in the EPROM. Instead of the EPROM, an EEPROM (Electrically Erasable Programmable ROM), a flash memory, or the like where data is electrically erasable may be used.

The control unit 5 is configured to include a data retaining unit 21 and a calculation unit 22.

The data retaining unit 21 retains data indicating the relationship between an appropriate column flow rate and the carrier gas flow rate. The data retaining unit 21 is configured as a portion of a memory 5a configured with, for example, an EPROM. In addition, the data retaining unit 21 may be included in a storage medium outside the microcomputer. The storage medium may be any storage medium which can retain the data indicating the relationship between appropriate column flow rate and the carrier gas flow rate. For example, the storage medium may be a hard disk drive (HDD), a solid state drive (SSD), a flexible disk (FD), an optical disk, a magneto-optical disk, a CD-ROM, a DVD-ROM, a DVD-RAM, a nonvolatile memory card, and the like.

The calculation unit 22 calculates the column flow rate on the basis of the analysis information input from the analysis information input unit 23. In addition, the calculation unit 22 calculates an appropriate carrier gas flow rate according to the calculated column flow rate from the calculated column flow rate and the value retained in the data retaining unit 21.

The analysis information input unit 23 is a unit with which, for example, the analysis information including an inner diameter, a length of the column 4, a temperature and a pressure applied to the column 4 are input. For example, the analysis information input from the analysis information input unit 23 is displayed on the display unit 24 by the calculation unit 22. In addition, information such as a carrier gas flow rate other than the above-described analysis information may be input from the analysis information input unit 23.

The relationship between the appropriate column flow rate and the carrier gas flow rate retained in the data retaining unit 21 may be a value obtained in advance by experiments or may be a value previously obtained by theoretical calculation or numerical calculation such as simulation.

In addition, in a case where the appropriate carrier gas flow rate is calculated by the calculation unit 22, only one value retained in the data retaining unit 21 may be used, or a plurality of values may be used.

The calculation of the column flow rate and the appropriate carrier gas flow rate by the calculation unit 22 is implemented by, for example, a program of the CPU. The data retaining unit 21 is data stored in the memory 5a connected to the CPU. The analysis information input unit 23 is, for example, an input device such as a keyboard or a touch panel connected to a CPU. The display unit 24 is, for example, a display device such as a monitor or a digital display connected to a CPU.

Figure 3:
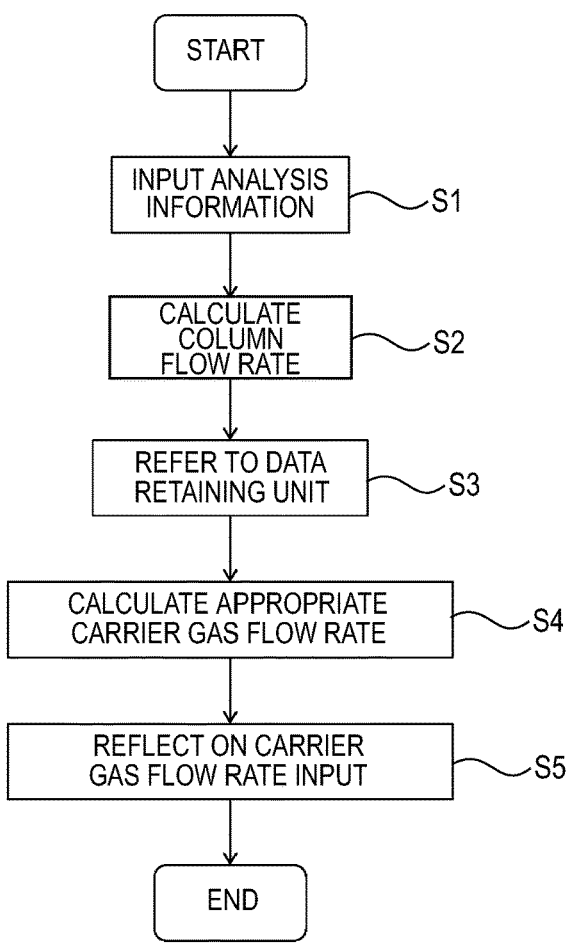
FIG. 3 is a flowchart for explaining a carrier gas flow rate calculation operation according to the embodiment.
Figure 4:
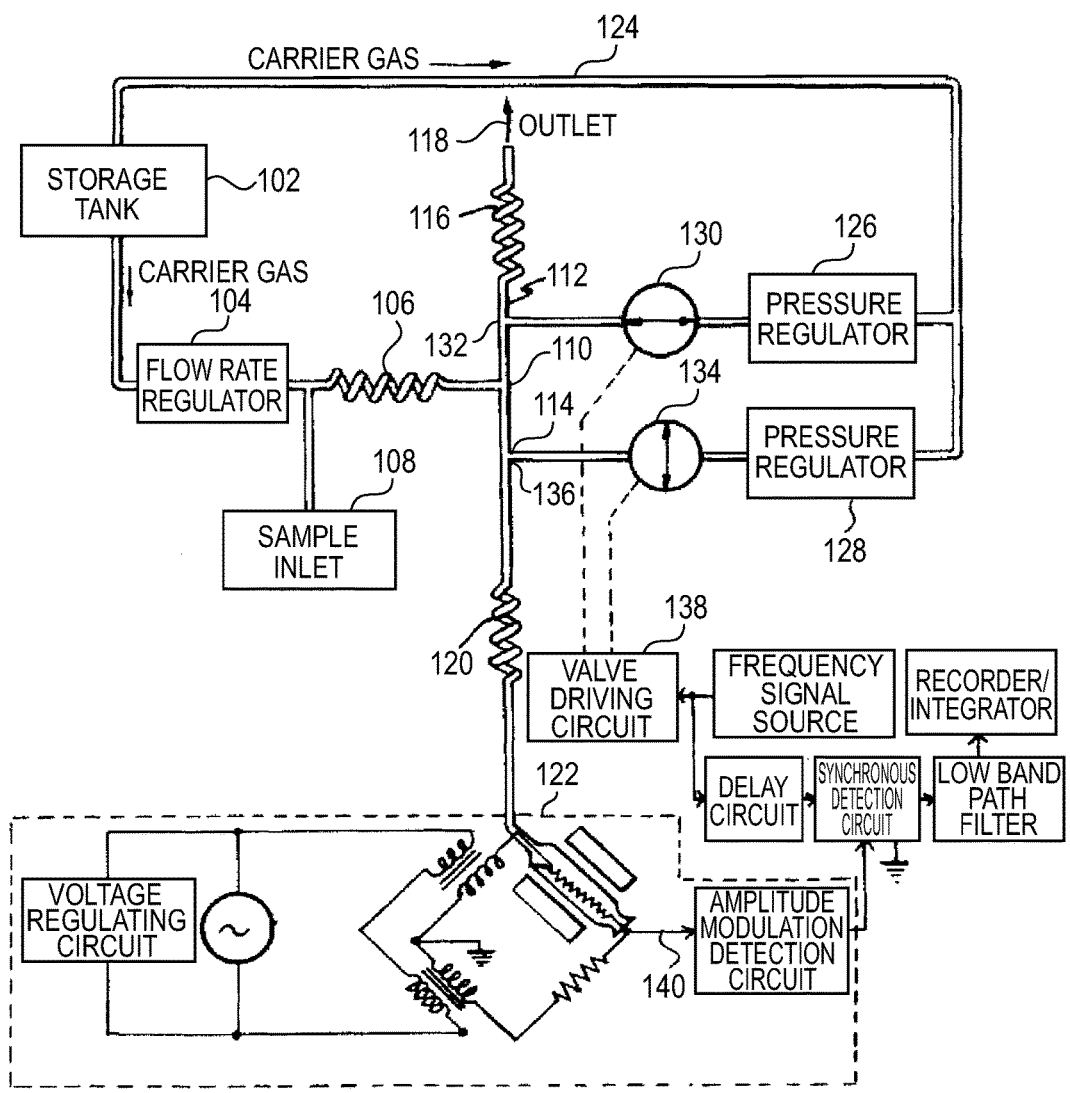
FIG. 4 is a block diagram illustrating an overall gas chromatograph in the related art.

FIG. 3 is a flowchart for explaining the carrier gas flow rate calculation operation according to the embodiment.

When the analysis information to be used in the gas chromatograph is input to the analysis information input unit 23 such as a keyboard (step S1), the calculation unit 22 calculates the column flow rate (step S2).

The calculation unit 22 refers to the data indicating the appropriate column flow rate and the carrier gas flow rate retained in the data retaining unit 21 (step S3). The appropriate carrier gas flow rate is calculated by the calculation unit 22 from the calculated column flow rate and the value retained in the data retaining unit 21 (step S4).

The calculated appropriate carrier gas flow rate is displayed on the display unit 24, provided to the operator by voice from the speaker, or provided to the operator by the both methods (step S5). Furthermore, the calculated appropriate carrier gas flow rate may be automatically input to the site where the carrier gas flow rate is input.

The control unit 5 controls the pressure regulator 7 on the basis of the value of the carrier gas flow rate displayed on the display unit 24.

In this manner, the chromatograph according to the embodiment automatically calculates the appropriate carrier gas flow rate and provides the appropriate carrier gas flow rate to the operator. Accordingly, it is possible to suppress dilution of the sample gas caused by the carrier gas and to improve the minimum detection amount.

Although the embodiments of the invention have been described above, the configurations, arrangements, numerical values, materials, and the like in the embodiments are merely examples, and the invention is not limited thereto. Various modifications can be made within the scope of the invention disclosed in the claims.

What is claimed is:

1. A gas chromatograph comprising:
   a column for separating a sample into components;
   a detector connected to downstream of the column, the detector including a detection unit for detecting the components of the sample separated by the column;
   first and second introducing channels which are each arranged to introduce a carrier gas into the detector;
   a switch for selecting one channel through which the carrier gas is introduced into the detector between the first introducing channel and the second introducing channel so that the carrier gas containing the components or the carrier gas alone is selectively introduced into the detector;
   a pressure regulator for regulating a flow rate of the carrier gas introduced into the detector through the first introducing channel or the second introducing channel;
   a control unit configured to control the pressure regulator;
   an analysis information input unit with which analysis information is input;
   a data retaining unit which retains data indicating a relationship between a preliminarily-set column flow rate and a carrier gas flow rate which is a flow rate of the carrier gas which is to be introduced into the detector; and
   a calculation unit which is configured to calculate the column flow rate on the basis of the analysis information input from the analysis information input unit and calculate the carrier gas flow rate according to the calculated column flow rate by using the calculated column flow rate and the data retained in the data retaining unit, wherein
   the control unit is configured to control the pressure regulator based on the calculated carrier gas flow rate.

2. The gas chromatograph according to claim 1, wherein the analysis information is at least one of an inner diameter of the column, a length of the column, a temperature, and a pressure applied to the column.

3. The gas chromatograph according to claim 1, wherein the gas chromatograph is configured to display the calculated carrier gas flow rate on a display unit, to input a carrier gas at the calculated carrier gas flow rate, or to perform both.

4. The gas chromatograph according to claim 2, wherein the gas chromatograph is configured to display the calculated carrier gas flow rate on a display unit, to input a carrier gas at the calculated carrier gas flow rate, or to perform both.

* * * * *